US008373001B2

(12) United States Patent
Rosier et al.

(10) Patent No.: US 8,373,001 B2
(45) Date of Patent: Feb. 12, 2013

(54) METHOD OF PRODUCING DINITRILE COMPOUNDS

(75) Inventors: Cécile Rosier, Soucieu en Jarrest (FR); Hocine Kabir, Serezin du Rhone (FR); Philippe Marion, Vernaison (FR)

(73) Assignee: Invista North America S.A R.L., Wilmington, DE (US)

( * ) Notice: Subject to any disclaimer, the term of this patent is extended or adjusted under 35 U.S.C. 154(b) by 1319 days.

(21) Appl. No.: 10/544,953

(22) PCT Filed: Jan. 22, 2004

(86) PCT No.: PCT/FR2004/000143
§ 371 (c)(1),
(2), (4) Date: Apr. 27, 2006

(87) PCT Pub. No.: WO2004/080924
PCT Pub. Date: Sep. 23, 2004

(65) Prior Publication Data
US 2006/0258873 A1 Nov. 16, 2006

(30) Foreign Application Priority Data

Feb. 10, 2003 (FR) ..................................... 03 01529

(51) Int. Cl.
*C07C 253/10* (2006.01)
*C07C 255/04* (2006.01)
(52) U.S. Cl. ....................................... 558/335; 558/456
(58) Field of Classification Search .................. 558/335, 558/456
See application file for complete search history.

(56) References Cited

U.S. PATENT DOCUMENTS

| | | | |
|---|---|---|---|
| 2,402,873 A | 6/1946 | Coffman et al. |
| 2,570,199 A | 10/1951 | Brown |
| 2,583,984 A | 1/1952 | Arthur, Jr. |
| 2,666,780 A | 1/1954 | Arthur, Jr. |
| 2,768,132 A | 10/1956 | Halliwell |
| 3,282,981 A | 11/1966 | Davis |
| 3,297,742 A | 1/1967 | Monroe, Jr. |
| 3,328,443 A | 6/1967 | Clark |
| 3,340,207 A | 9/1967 | Baker |
| 3,370,082 A | 2/1968 | Eisfeld et al. |
| 3,496,210 A | 2/1970 | Drinkard, Jr. |
| 3,496,215 A | 2/1970 | Drinkard et al. |
| 3,496,217 A | 2/1970 | Drinkard, Jr. et al. |
| 3,496,218 A | 2/1970 | Drinkard, Jr. |
| 3,522,288 A | 7/1970 | Drinkard, Jr. et al. |
| 3,526,654 A | 9/1970 | Hildebrand |
| 3,536,748 A | 10/1970 | Drinkard, Jr. et al. |
| 3,538,142 A | 11/1970 | Drinkard, Jr. |
| 3,542,847 A | 11/1970 | Drinkard, Jr. |
| 3,547,972 A | 12/1970 | Drinkard, Jr. |
| 3,551,474 A | 12/1970 | Drinkard et al. |
| 3,563,698 A | 2/1971 | Rushmere |
| 3,564,040 A | 2/1971 | Downing et al. |
| 3,579,560 A | 5/1971 | Drinkard et al. |
| 3,631,191 A | 12/1971 | Kane |
| 3,641,107 A | 2/1972 | Breda |
| 3,651,146 A | 3/1972 | Schriltz |
| 3,652,641 A | 3/1972 | Druliner |
| 3,655,723 A | 4/1972 | Drinkard, Jr. et al. |
| 3,676,475 A | 7/1972 | Drinkard, Jr. |
| 3,676,481 A | 7/1972 | Chia |
| 3,694,485 A | 9/1972 | Drinkard, Jr. et al. |
| 3,739,011 A | 6/1973 | Drinkard |
| 3,752,839 A | 8/1973 | Drinkard, Jr. et al. |
| 3,766,231 A | 10/1973 | Gosser et al. |
| 3,766,237 A | 10/1973 | Chia et al. |
| 3,766,241 A | 10/1973 | Drinkard, Jr. et al. |
| 3,773,809 A | 11/1973 | Walter |
| 3,775,461 A | 11/1973 | Drinkard, Jr. et al. |
| 3,798,256 A | 3/1974 | King et al. |
| 3,818,067 A | 6/1974 | Downing et al. |
| 3,818,068 A | 6/1974 | Wells |
| 3,846,461 A | 11/1974 | Shook |
| 3,846,474 A | 11/1974 | Mok |
| 3,847,959 A | 11/1974 | Shook |
| 3,849,472 A | 11/1974 | Waddan |
| 3,850,973 A | 11/1974 | Seidel et al. |
| 3,852,325 A | 12/1974 | King |
| 3,852,327 A | 12/1974 | Druliner |

(Continued)

FOREIGN PATENT DOCUMENTS

| AU | 6522096 | 2/1997 |
|---|---|---|
| AU | 199665220 A | 2/1997 |

(Continued)

OTHER PUBLICATIONS

Romanovski et al. "Potential Agenst for Removal of Actinides from Waste Solutions" Preprint for the Spectrum '96 International Conference on Nuclear and Hazardous Waste Management Conference Proceedings, 1996, the whole document.*

Summary Report: Control and Treatment Technology for the Metal Finishing Industry—Ion Exchange USEPA EPA 625/-81-007 Jun. 1981 pp. 4-10.*

Rohm and Haas Company "Ion Exchange Resins for Chemical Processing" 2001.*

Croxtall et al. "Separation, recovery and recycling of a fluorous-tagged nickel catalyst using fluorous solid-phase extraction" Chemical Communications, 2003, pp. 2430-2431.*

(Continued)

*Primary Examiner* — Joseph Kosack

(57) ABSTRACT

The present invention relates to a process for the manufacture of compounds comprising two nitrile functional groups. It relates more particularly to a process for the manufacture of dinitrile compounds from compounds comprising a nitrile functional group and an ethylenic unsaturation in the presence of a catalytic system comprising an organometallic complex and a cocatalyst of the Lewis acid type. The process of the invention comprises a stage of treatment of the reaction medium resulting from the hydrocyanation which makes it possible to extract and recover the metal element of the Lewis acid.

20 Claims, No Drawings

U.S. PATENT DOCUMENTS

| | | | |
|---|---|---|---|
| 3,852,328 A | 12/1974 | Chia |
| 3,852,329 A | 12/1974 | Tomlinson |
| 3,853,754 A | 12/1974 | Gosser |
| 3,853,948 A | 12/1974 | Drinkard, Jr. et al. |
| 3,859,327 A | 1/1975 | Wells |
| 3,864,380 A | 2/1975 | King et al. |
| 3,865,865 A | 2/1975 | Musser |
| 3,869,501 A | 3/1975 | Waddan |
| 3,884,997 A | 5/1975 | Shook, Jr. |
| 3,903,120 A | 9/1975 | Shook, Jr. |
| 3,920,721 A | 11/1975 | Gosser |
| 3,925,445 A | 12/1975 | King |
| 3,927,056 A | 12/1975 | Gosser |
| 3,947,487 A | 3/1976 | Crooks |
| 3,983,011 A | 9/1976 | Wiggill |
| 3,997,579 A | 12/1976 | Jesson |
| 4,045,495 A | 8/1977 | Nazarenko et al. |
| 4,046,815 A | 9/1977 | Nazarenko |
| 4,076,756 A | 2/1978 | Nazarenko et al. |
| 4,080,374 A | 3/1978 | Corn |
| 4,082,811 A | 4/1978 | Shook, Jr. |
| 4,087,452 A | 5/1978 | Kuntz |
| 4,123,379 A * | 10/1978 | Gates et al. ............ 502/159 |
| 4,134,923 A | 1/1979 | Reimer |
| 4,146,555 A | 3/1979 | Kershaw |
| 4,147,717 A | 4/1979 | Kershaw |
| 4,177,215 A | 12/1979 | Seidel |
| 4,210,558 A | 7/1980 | Crooks |
| 4,230,634 A | 10/1980 | Benzie et al. |
| 4,240,976 A | 12/1980 | Benzie et al. |
| 4,251,468 A | 2/1981 | Nazarenko |
| 4,298,546 A | 11/1981 | Mc Gill |
| 4,328,172 A | 5/1982 | Rapoport |
| 4,330,483 A | 5/1982 | Rapoport |
| 4,336,110 A | 6/1982 | Reimer |
| 4,339,395 A | 7/1982 | Barnette et al. |
| 4,347,193 A | 8/1982 | Shook, Jr. |
| 4,371,474 A | 2/1983 | Rapoport |
| 4,382,038 A | 5/1983 | McGill |
| 4,385,007 A | 5/1983 | Shook, Jr. |
| 4,387,056 A | 6/1983 | Stowe |
| 4,394,321 A | 7/1983 | Cone |
| 4,416,824 A | 11/1983 | Reimer et al. |
| 4,416,825 A | 11/1983 | Ostermaier |
| 4,434,316 A | 2/1984 | Barnette |
| 4,510,327 A | 4/1985 | Peet |
| 4,521,628 A | 6/1985 | Ostermaier |
| 4,539,302 A | 9/1985 | Leyendecker et al. |
| 4,705,881 A | 11/1987 | Rapoport |
| 4,714,773 A | 12/1987 | Rapoport |
| 4,749,801 A | 6/1988 | Beatty et al. |
| 4,774,353 A | 9/1988 | Hall et al. |
| 4,783,546 A | 11/1988 | Burke |
| 4,810,815 A | 3/1989 | Bryndza |
| 4,874,884 A | 10/1989 | McKinney et al. |
| 4,990,645 A | 2/1991 | Back et al. |
| 5,087,723 A | 2/1992 | Mc Kinney |
| 5,107,012 A | 4/1992 | Grunewald |
| 5,143,873 A | 9/1992 | Bryndza |
| 5,175,335 A | 12/1992 | Casalnuovo |
| 5,302,756 A | 4/1994 | McKinney |
| 5,312,957 A | 5/1994 | Casalnuovo |
| 5,312,959 A | 5/1994 | Sieja et al. |
| 5,382,697 A | 1/1995 | Casalnuovo |
| 5,440,067 A | 8/1995 | Druliner |
| 5,449,807 A | 9/1995 | Druliner |
| 5,484,902 A | 1/1996 | Casalnuovo |
| 5,488,129 A | 1/1996 | Huser et al. |
| 5,510,470 A | 4/1996 | Casalnuovo |
| 5,512,695 A | 4/1996 | Kreutzer et al. |
| 5,512,696 A | 4/1996 | Kreutzer et al. |
| 5,523,453 A | 6/1996 | Breikss |
| 5,543,536 A | 8/1996 | Tam |
| 5,663,369 A | 9/1997 | Kreutzer et al. |
| 5,688,986 A | 11/1997 | Tam et al. |
| 5,693,843 A | 12/1997 | Breikss |
| 5,696,280 A | 12/1997 | Shapiro |
| 5,709,841 A | 1/1998 | Reimer |
| 5,723,641 A | 3/1998 | Tam et al. |
| 5,773,637 A | 6/1998 | Cicha et al. |
| 5,821,378 A | 10/1998 | Foo et al. |
| 5,847,191 A | 12/1998 | Bunel et al. |
| 5,856,555 A | 1/1999 | Huser et al. |
| 5,908,805 A | 6/1999 | Huser et al. |
| 5,959,135 A * | 9/1999 | Garner et al. ............ 558/338 |
| 5,981,772 A | 11/1999 | Foo |
| 6,020,516 A | 2/2000 | Foo |
| 6,031,120 A | 2/2000 | Tam |
| 6,048,996 A | 4/2000 | Clarkson |
| 6,069,267 A | 5/2000 | Tam |
| 6,077,979 A | 6/2000 | Qiu |
| 6,090,987 A | 7/2000 | Billig et al. |
| 6,120,700 A | 9/2000 | Foo |
| 6,121,184 A | 9/2000 | Druliner et al. |
| 6,127,567 A | 10/2000 | Garner |
| 6,147,247 A | 11/2000 | Voit et al. |
| 6,169,198 B1 | 1/2001 | Fischer et al. |
| 6,171,996 B1 | 1/2001 | Garner et al. |
| 6,171,997 B1 | 1/2001 | Foo |
| 6,197,992 B1 | 3/2001 | Fischer et al. |
| 6,207,851 B1 | 3/2001 | Bassler et al. |
| 6,242,633 B1 | 6/2001 | Fischer et al. |
| 6,284,865 B1 | 9/2001 | Tam et al. |
| 6,307,109 B1 | 10/2001 | Kanel et al. |
| 6,355,833 B2 | 3/2002 | Fischer et al. |
| 6,362,354 B1 | 3/2002 | Bunel |
| 6,372,147 B1 | 4/2002 | Reimer |
| 6,380,421 B1 | 4/2002 | Lu |
| 6,399,534 B2 | 6/2002 | Bunel |
| 6,420,611 B1 | 7/2002 | Tam |
| 6,461,481 B1 | 10/2002 | Barnette et al. |
| 6,469,194 B2 * | 10/2002 | Burattin et al. ............ 558/338 |
| 6,489,517 B1 | 12/2002 | Shapiro |
| 6,521,778 B1 | 2/2003 | Fischer et al. |
| 6,555,718 B1 | 4/2003 | Shapiro |
| 6,646,148 B1 | 11/2003 | Kreutzer |
| 6,660,876 B2 | 12/2003 | Gagne |
| 6,660,877 B2 | 12/2003 | Lenges et al. |
| 6,737,539 B2 | 5/2004 | Lenges et al. |
| 6,753,440 B2 | 6/2004 | Druliner et al. |
| 6,770,770 B1 | 8/2004 | Baumann et al. |
| 6,812,352 B2 | 11/2004 | Kreutzer |
| 6,844,289 B2 | 1/2005 | Jackson |
| 6,846,945 B2 | 1/2005 | Lenges et al. |
| 6,852,199 B2 | 2/2005 | Jungkamp et al. |
| 6,855,799 B2 | 2/2005 | Tam et al. |
| 6,893,996 B2 | 5/2005 | Chu |
| 6,897,329 B2 | 5/2005 | Jackson et al. |
| 6,906,218 B2 | 6/2005 | Allgeier |
| 6,924,345 B2 | 8/2005 | Gagne |
| 6,936,171 B2 | 8/2005 | Jackson |
| 6,984,604 B2 | 1/2006 | Cobb et al. |
| 7,022,866 B2 | 4/2006 | Bartsch et al. |
| 7,067,685 B2 | 6/2006 | Bartsch et al. |
| 7,071,365 B2 | 7/2006 | Lu |
| 7,084,293 B2 | 8/2006 | Rosier et al. |
| 7,084,294 B2 | 8/2006 | Jungkamp et al. |
| 7,098,358 B2 | 8/2006 | Burattin et al. |
| 7,105,696 B2 | 9/2006 | Burattin et al. |
| 7,253,298 B2 | 8/2007 | Galland et al. |
| 7,345,006 B2 | 3/2008 | Bartsch et al. |
| 7,381,845 B2 | 6/2008 | Weiskopf et al. |
| 7,439,381 B2 | 10/2008 | Jungkamp et al. |
| 7,442,825 B2 | 10/2008 | Galland et al. |
| 7,470,805 B2 | 12/2008 | Rosier et al. |
| 7,521,575 B2 | 4/2009 | Bartsch et al. |
| 7,528,275 B2 | 5/2009 | Bartsch et al. |
| 7,538,240 B2 | 5/2009 | Jungkamp et al. |
| 7,541,486 B2 | 6/2009 | Scheidel et al. |
| 7,700,795 B2 | 4/2010 | Haderlein et al. |
| 2003/0100802 A1 | 5/2003 | Shapiro |
| 2003/0135014 A1 | 7/2003 | Radu et al. |
| 2003/0212298 A1 | 11/2003 | Brasse et al. |
| 2004/0063991 A1 | 4/2004 | Burattin et al. |
| 2004/0106815 A1 | 6/2004 | Ritter |
| 2004/0176622 A1 | 9/2004 | Bartsch et al. |
| 2004/0235648 A1 | 11/2004 | Bartsch et al. |

| | | | |
|---|---|---|---|
| 2004/0260112 A1 | 12/2004 | Basset et al. | |
| 2005/0059737 A1 | 3/2005 | Allgeier | |
| 2005/0090677 A1 | 4/2005 | Bartsch et al. | |
| 2005/0090678 A1 | 4/2005 | Bartsch et al. | |
| 2005/0159614 A1 | 7/2005 | Allgeier | |
| 2005/0247624 A1 | 11/2005 | Jungkamp et al. | |
| 2006/0142609 A1 | 6/2006 | Bourgeois et al. | |
| 2006/0175189 A1 | 8/2006 | Gerber et al. | |
| 2006/0252955 A1 | 11/2006 | Rosier et al. | |
| 2006/0258873 A1 | 11/2006 | Rosier et al. | |
| 2006/0258874 A1 | 11/2006 | Bartsch et al. | |
| 2006/0264651 A1 | 11/2006 | Bartsch et al. | |
| 2007/0060766 A1 | 3/2007 | Bartsch et al. | |
| 2007/0073071 A1 | 3/2007 | Haderlein et al. | |
| 2007/0083057 A1 | 4/2007 | Haderlein et al. | |
| 2007/0088173 A1 | 4/2007 | Haderlein et al. | |
| 2007/0112215 A1 | 5/2007 | Jungkamp et al. | |
| 2007/0155977 A1 | 7/2007 | Jungkamp et al. | |
| 2007/0155978 A1 | 7/2007 | Jungkamp et al. | |
| 2007/0155980 A1 | 7/2007 | Scheidel et al. | |
| 2007/0219386 A1 | 9/2007 | Ritter | |
| 2008/0015378 A1 | 1/2008 | Foo et al. | |
| 2008/0015379 A1 | 1/2008 | Garner | |
| 2008/0015380 A1 | 1/2008 | Foo et al. | |
| 2008/0015381 A1 | 1/2008 | Foo et al. | |
| 2008/0015382 A1 | 1/2008 | Foo et al. | |
| 2008/0071105 A1 | 3/2008 | Bartsch et al. | |
| 2008/0076944 A1 | 3/2008 | Bartsch et al. | |
| 2008/0083607 A1 | 4/2008 | Deckert et al. | |
| 2008/0221351 A1 | 9/2008 | Bartsch et al. | |
| 2008/0227214 A1 | 9/2008 | Jungkamp et al. | |
| 2008/0227998 A1 | 9/2008 | Scheidel et al. | |
| 2008/0242883 A1 | 10/2008 | Jungkamp et al. | |
| 2008/0242885 A1 | 10/2008 | Jungkamp et al. | |
| 2008/0242886 A1 | 10/2008 | Bartsch et al. | |
| 2008/0275266 A1 | 11/2008 | Bartsch et al. | |
| 2008/0281119 A1 | 11/2008 | Scheidel et al. | |
| 2008/0281120 A1 | 11/2008 | Jungkamp et al. | |
| 2009/0054671 A1 | 2/2009 | Haderlein et al. | |

FOREIGN PATENT DOCUMENTS

| | | | |
|---|---|---|---|
| CA | 1324613 C | 11/1993 | |
| CA | 2462720 A1 | 4/2003 | |
| CA | 2552862 A1 | 8/2005 | |
| CN | 1113854 A | 12/1995 | |
| CN | 1145531 A | 3/1997 | |
| CN | 1146166 A | 3/1997 | |
| CN | 1146762 A | 4/1997 | |
| CN | 1159106 A | 9/1997 | |
| CN | 1159799 A | 9/1997 | |
| CN | 1163606 A | 10/1997 | |
| CN | 1169143 A | 12/1997 | |
| CN | 1173935 A | 2/1998 | |
| CN | 1179147 A | 4/1998 | |
| CN | 1198151 A | 11/1998 | |
| CN | 1204111 A | 1/1999 | |
| CN | 1206357 A | 1/1999 | |
| CN | 1211931 A | 3/1999 | |
| CN | 1045591 C | 10/1999 | |
| CN | 1236355 A | 11/1999 | |
| CN | 1047163 C | 12/1999 | |
| CN | 1245489 A | 2/2000 | |
| CN | 1247102 A | 3/2000 | |
| CN | 1052718 C | 5/2000 | |
| CN | 1265094 A | 8/2000 | |
| CN | 1266424 A | 9/2000 | |
| CN | 1270543 A | 10/2000 | |
| CN | 1068307 C | 7/2001 | |
| CN | 1304334 A | 7/2001 | |
| CN | 1069310 C | 8/2001 | |
| CN | 1072980 C | 10/2001 | |
| CN | 1076342 C | 12/2001 | |
| CN | 1327881 A | 12/2001 | |
| CN | 1331843 A | 1/2002 | |
| CN | 1333745 A | 1/2002 | |
| CN | 1082946 C | 4/2002 | |
| CN | 1344180 A | 4/2002 | |
| CN | 1356335 A | 7/2002 | |
| CN | 1387534 A | 12/2002 | |
| CN | 1099912 C | 1/2003 |
| CN | 1390241 A | 1/2003 |
| CN | 1103613 C | 3/2003 |
| CN | 1106218 C | 4/2003 |
| CN | 1108643 C | 5/2003 |
| CN | 1427807 A | 7/2003 |
| CN | 1449400 A | 10/2003 |
| CN | 1461295 A | 12/2003 |
| CN | 1471510 A | 1/2004 |
| CN | 1141285 C | 3/2004 |
| CN | 1142224 C | 3/2004 |
| CN | 1144781 C | 4/2004 |
| CN | 1487917 A | 4/2004 |
| CN | 1152855 C | 6/2004 |
| CN | 1535179 A | 10/2004 |
| CN | 1564807 A | 1/2005 |
| CN | 1568225 A | 1/2005 |
| CN | 1568226 A | 1/2005 |
| CN | 1617892 A | 5/2005 |
| CN | 1617900 A | 5/2005 |
| CN | 1212293 C | 7/2005 |
| CN | 1639176 A | 7/2005 |
| CN | 1213051 C | 8/2005 |
| CN | 1665776 A | 9/2005 |
| CN | 1670139 A | 9/2005 |
| CN | 1674989 A | 9/2005 |
| CN | 1675172 A | 9/2005 |
| CN | 1222358 C | 10/2005 |
| CN | 1732148 A | 2/2006 |
| CN | 1735460 A | 2/2006 |
| CN | 1245489 C | 3/2006 |
| CN | 1740183 A | 3/2006 |
| CN | 1745062 A | 3/2006 |
| CN | 1767895 A | 5/2006 |
| CN | 1260009 C | 6/2006 |
| CN | 1266424 C | 7/2006 |
| CN | 1270543 C | 8/2006 |
| CN | 1274671 C | 9/2006 |
| CN | 1274699 C | 9/2006 |
| CN | 1835915 A | 9/2006 |
| CN | 1279088 C | 10/2006 |
| CN | 1847288 A | 10/2006 |
| CN | 1283620 C | 11/2006 |
| CN | 1857775 A | 11/2006 |
| CN | 1289539 C | 12/2006 |
| CN | 1293942 C | 1/2007 |
| CN | 1906150 A | 1/2007 |
| CN | 1914154 A | 2/2007 |
| CN | 1914155 A | 2/2007 |
| CN | 1914156 A | 2/2007 |
| CN | 1914157 A | 2/2007 |
| CN | 1914158 A | 2/2007 |
| CN | 1914159 A | 2/2007 |
| CN | 1914160 A | 2/2007 |
| CN | 1914161 A | 2/2007 |
| CN | 1914162 A | 2/2007 |
| CN | 1914165 A | 2/2007 |
| CN | 1914166 A | 2/2007 |
| CN | 1914167 A | 2/2007 |
| CN | 1914216 A | 2/2007 |
| CN | 1307237 C | 3/2007 |
| CN | 1315790 C | 5/2007 |
| CN | 1318432 C | 5/2007 |
| CN | 1997624 A | 7/2007 |
| CN | 1331843 C | 8/2007 |
| CN | 101020641 A | 8/2007 |
| CN | 101035799 A | 9/2007 |
| CN | 101043946 A | 9/2007 |
| CN | 100348322 C | 11/2007 |
| CN | 100351227 C | 11/2007 |
| CN | 100352824 C | 12/2007 |
| CN | 100361966 C | 1/2008 |
| CN | 100364666 C | 1/2008 |
| DE | 1807088 U | 3/1960 |
| DE | 1807088 A1 | 6/1969 |
| DE | 2055747 A1 | 5/1971 |
| DE | 1593277 B2 | 8/1973 |
| DE | 1593277 C3 | 3/1974 |
| DE | 2700904 C2 | 10/1983 |

| | | | | | | |
|---|---|---|---|---|---|---|
| DE | 68909466 | T2 | 3/1994 | EP | 1448620 B1 | 6/2008 |
| DE | 10136488 | A1 | 2/2003 | EP | 1817108 B1 | 6/2008 |
| DE | 10150285 | A1 | 4/2003 | EP | 1713760 B1 | 7/2008 |
| DE | 10350999 | A1 | 6/2005 | EP | 1571172 B1 | 10/2008 |
| DE | 102004004696 | A1 | 8/2005 | EP | 1988998 A1 | 11/2008 |
| EP | 0001899 | B1 | 3/1982 | EP | 1265832 B1 | 5/2009 |
| EP | 123438 | B1 | 7/1987 | EP | 1592659 B1 | 7/2009 |
| EP | 160296 | B1 | 10/1988 | EP | 1586598 B1 | 9/2009 |
| EP | 268448 | B1 | 9/1991 | EP | 2098106 A1 | 9/2009 |
| EP | 510689 | A1 | 10/1992 | EP | 1567478 B1 | 10/2009 |
| EP | 248643 | B1 | 3/1993 | EP | 1682559 B1 | 12/2009 |
| EP | 336314 | B1 | 9/1993 | EP | 1630166 B1 | 2/2010 |
| EP | 464691 | B1 | 12/1993 | FR | 154456 A | 11/1968 |
| EP | 675871 | B1 | 4/1997 | FR | 2015115 A5 | 4/1970 |
| EP | 634395 | B1 | 9/1997 | FR | 1603513 A | 5/1971 |
| EP | 650959 | B1 | 9/1997 | FR | 2069411 A5 | 9/1971 |
| EP | 784610 | B1 | 2/1999 | FR | 2845379 B1 | 12/2004 |
| EP | 757672 | B1 | 6/1999 | FR | 2873696 A1 | 2/2006 |
| EP | 792259 | B1 | 8/1999 | FR | 2873696 B1 | 10/2006 |
| EP | 804412 | B1 | 12/1999 | GB | 0219474 A | 7/1924 |
| EP | 1000019 | A1 | 5/2000 | GB | 1104140 A | 2/1968 |
| EP | 1001928 | A1 | 5/2000 | GB | 1203702 A | 9/1970 |
| EP | 1003716 | A1 | 5/2000 | GB | 1213175 A | 11/1970 |
| EP | 1019190 | A1 | 7/2000 | GB | 1429169 A | 3/1976 |
| EP | 755302 | B1 | 10/2000 | GB | 1429621 A | 3/1976 |
| EP | 929513 | B1 | 4/2001 | GB | 1436932 A | 5/1976 |
| EP | 881924 | B1 | 5/2001 | GB | 1458322 A | 12/1976 |
| EP | 854858 | B1 | 6/2001 | GB | 1482909 A | 8/1977 |
| EP | 815073 | B1 | 7/2001 | GB | 2007521 A | 5/1979 |
| EP | 1144114 | A3 | 9/2001 | GB | 1565443 A | 4/1980 |
| EP | 1091804 | B1 | 2/2002 | GB | 1594694 A | 8/1981 |
| EP | 944585 | B1 | 4/2002 | GB | 2007521 B | 6/1982 |
| EP | 1000019 | B1 | 2/2003 | GB | 2 212 155 A | 7/1989 |
| EP | 911339 | B1 | 4/2003 | HK | 1025950 A1 | 7/2003 |
| EP | 1216268 | B1 | 11/2003 | HK | 1026383 A1 | 7/2004 |
| EP | 1350788 | A3 | 11/2003 | HK | 1052364 A1 | 5/2007 |
| EP | 1003607 | B1 | 12/2003 | JP | 48028423 Y1 | 8/1973 |
| EP | 1003716 | B1 | 2/2004 | JP | 48028423 B | 9/1973 |
| EP | 1313743 | B1 | 3/2004 | JP | 49043924 Y1 | 12/1974 |
| EP | 1414567 | A1 | 5/2004 | JP | 50059324 U | 6/1975 |
| EP | 1427695 | A1 | 6/2004 | JP | 50059326 U | 6/1975 |
| EP | 1438133 | A1 | 7/2004 | JP | 51007649 B | 3/1976 |
| EP | 1019190 | B1 | 12/2004 | JP | 52012698 B | 4/1977 |
| EP | 1140801 | B1 | 2/2005 | JP | 1013127 C | 9/1980 |
| EP | 1395547 | B1 | 3/2005 | JP | 55047031 B | 11/1980 |
| EP | 1001928 | B1 | 4/2005 | JP | 57156454 U | 10/1982 |
| EP | 1521736 | A1 | 4/2005 | JP | 57156455 U | 10/1982 |
| EP | 1521737 | A1 | 4/2005 | JP | 57179144 U | 11/1982 |
| EP | 1521738 | A2 | 4/2005 | JP | 1136333 C | 2/1983 |
| EP | 1603865 | A1 | 12/2005 | JP | 58067658 U | 5/1983 |
| EP | 1324976 | B1 | 2/2006 | JP | 58126892 U | 8/1983 |
| EP | 1214975 | B1 | 3/2006 | JP | 1170710 C | 10/1983 |
| EP | 1324978 | B1 | 3/2006 | JP | 58159452 U | 10/1983 |
| EP | 1648860 | A1 | 4/2006 | JP | 60044295 A | 3/1985 |
| EP | 891323 | B1 | 6/2006 | JP | 60044295 B | 10/1985 |
| EP | 1226147 | B1 | 6/2006 | JP | 62294691 A | 12/1987 |
| EP | 1438317 | B1 | 6/2006 | JP | 63135363 U | 9/1988 |
| EP | 1682561 | A1 | 7/2006 | JP | 1013127 Y2 | 4/1989 |
| EP | 1448668 | B1 | 8/2006 | JP | 1209830 A | 8/1989 |
| EP | 1587621 | B1 | 8/2006 | JP | 1136333 U | 9/1989 |
| EP | 1713759 | A1 | 10/2006 | JP | 1050220 B | 10/1989 |
| EP | 1713761 | A1 | 10/2006 | JP | 1173751 U | 12/1989 |
| EP | 1713762 | A1 | 10/2006 | JP | 1565159 C | 6/1990 |
| EP | 1713766 | A1 | 10/2006 | JP | 3001298 B | 1/1991 |
| EP | 1716102 | A2 | 11/2006 | JP | 1615749 C | 8/1991 |
| EP | 1716103 | A1 | 11/2006 | JP | 3205587 A | 9/1991 |
| EP | 1716104 | A1 | 11/2006 | JP | 1627124 C | 11/1991 |
| EP | 1716105 | A1 | 11/2006 | JP | 1627146 C | 11/1991 |
| EP | 1716106 | A1 | 11/2006 | JP | 3069915 B | 11/1991 |
| EP | 1716107 | A1 | 11/2006 | JP | 3285878 A | 12/1991 |
| EP | 1716109 | A2 | 11/2006 | JP | 1642102 C | 2/1992 |
| EP | 1610893 | B1 | 3/2007 | JP | 4012248 Y2 | 3/1992 |
| EP | 1621531 | B1 | 3/2007 | JP | 4057050 U | 5/1992 |
| EP | 1438132 | B1 | 4/2007 | JP | 4166155 A | 6/1992 |
| EP | WO2007051374 | A1 | 5/2007 | JP | 4230254 A | 8/1992 |
| EP | 1799697 | A1 | 6/2007 | JP | 4057050 B | 9/1992 |
| EP | 1713764 | B1 | 8/2007 | JP | 4060532 B | 9/1992 |
| EP | 1713816 | B1 | 8/2007 | JP | 4118676 U | 10/1992 |
| EP | 1825914 | A1 | 8/2007 | JP | 4128141 U | 11/1992 |

| | | | | | | | |
|---|---|---|---|---|---|---|---|
| JP | 1729140 | C | 1/1993 | JP | 04057050 | B2 | 3/2008 |
| JP | 1811422 | C | 12/1993 | JP | 04060532 | B2 | 3/2008 |
| JP | 7025841 | Y2 | 6/1995 | JP | 2006512918X | | 3/2008 |
| JP | 7188144 | A | 7/1995 | JP | 2008515831 | A | 5/2008 |
| JP | 2037346 | C | 3/1996 | JP | 20085169907 | A | 5/2008 |
| JP | 8504814 | A | 5/1996 | JP | 04118676 | B2 | 7/2008 |
| JP | 8157795 | A | 6/1996 | JP | 04128141 | B2 | 7/2008 |
| JP | 2098106 | C | 10/1996 | JP | 04166155 | B2 | 10/2008 |
| JP | 02521777 | Y2 | 1/1997 | JP | 04230254 | B2 | 2/2009 |
| JP | 02623448 | B2 | 6/1997 | KR | 198802621 | Y1 | 7/1988 |
| JP | 9505586 | A | 6/1997 | KR | 198802296 | B | 10/1988 |
| JP | 9512013 | A | 12/1997 | KR | 198802296 | B1 | 10/1988 |
| JP | 10505101 | A | 5/1998 | KR | 199003458 | B1 | 5/1990 |
| JP | 10506911 | A | 7/1998 | KR | 19908166 | B1 | 11/1990 |
| JP | 10509954 | A | 9/1998 | KR | 199104132 | B1 | 6/1991 |
| JP | 02818503 | B2 | 10/1998 | KR | 199205087 | Y1 | 7/1992 |
| JP | 10512879 | A | 12/1998 | KR | 2006132885 | A | 12/2006 |
| JP | 11501660 | A | 2/1999 | MX | 2004PA002764 | A | 6/2004 |
| JP | 11504262 | A | 4/1999 | NL | 197700262 | A | 7/1977 |
| JP | 02911608 | B2 | 6/1999 | NL | 188158 | C | 4/1992 |
| JP | 11507297 | A | 6/1999 | SU | 677650 | A | 7/1979 |
| JP | 03001298 | B2 | 1/2000 | TW | 387874 | B | 4/2000 |
| JP | 03069915 | B2 | 7/2000 | TW | 400249 | B | 8/2000 |
| JP | 2001500135 | A | 1/2001 | TW | 453983 | B | 9/2001 |
| JP | 2001506250 | A | 5/2001 | TW | 453985 | B | 9/2001 |
| JP | 2001512097 | A | 8/2001 | TW | 455576 | B | 9/2001 |
| JP | 03205587 | B2 | 9/2001 | TW | 457244 | B | 10/2001 |
| JP | 2001516640 | A | 10/2001 | TW | 458959 | B | 10/2001 |
| JP | 03285878 | B2 | 5/2002 | TW | 519496 | B | 2/2003 |
| JP | 2002517473 | A | 6/2002 | TW | 527340 | B | 4/2003 |
| JP | 03320424 | B2 | 9/2002 | TW | 576837 | B | 2/2004 |
| JP | 2002533321 | A | 10/2002 | TW | 580489 | B | 3/2004 |
| JP | 03380543 | B2 | 2/2003 | TW | 580490 | B | 3/2004 |
| JP | 2003510385 | A | 3/2003 | TW | 584623 | B | 4/2004 |
| JP | 2003526688 | A | 9/2003 | TW | 592821 | B | 6/2004 |
| JP | 03478399 | B2 | 12/2003 | TW | 226345 | B | 1/2005 |
| JP | 2004501058 | A | 1/2004 | TW | 233438 | B | 6/2005 |
| JP | 2004507550 | A | 3/2004 | TW | 245780 | B | 12/2005 |
| JP | 03519410 | B2 | 4/2004 | TW | 266650 | B | 11/2006 |
| JP | 03535172 | B2 | 6/2004 | WO | WO7900193 | A1 | 4/1979 |
| JP | 03553952 | B2 | 8/2004 | WO | WO9414752 | A1 | 7/1994 |
| JP | 2004534032 | A | 11/2004 | WO | WO9514659 | A1 | 6/1995 |
| JP | 2004535929 | A | 12/2004 | WO | WO9528228 | A1 | 10/1995 |
| JP | 03621133 | B2 | 2/2005 | WO | WO9529153 | A1 | 11/1995 |
| JP | 2005503410 | A | 2/2005 | WO | WO9611182 | A1 | 4/1996 |
| JP | 2005505610 | A | 2/2005 | WO | WO9616022 | A1 | 5/1996 |
| JP | 2005505611 | A | 2/2005 | WO | WO9622968 | A1 | 8/1996 |
| JP | 2005510588 | A | 4/2005 | WO | WO9629303 | A1 | 9/1996 |
| JP | 2005510605 | A | 4/2005 | WO | WO9703040 | A1 | 1/1997 |
| JP | 2004509942X | | 10/2005 | WO | WO9712857 | A1 | 4/1997 |
| JP | 2005533095 | A | 11/2005 | WO | WO9724183 | A1 | 7/1997 |
| JP | 2005533096 | A | 11/2005 | WO | WO9736855 | A2 | 10/1997 |
| JP | 2005538075 | A | 12/2005 | WO | WO9811051 | A1 | 3/1998 |
| JP | 03739404 | B2 | 1/2006 | WO | WO9827054 | A1 | 6/1998 |
| JP | 2004534032X | | 1/2006 | WO | WO 99/06356 | A | 2/1999 |
| JP | 2004535929X | | 1/2006 | WO | WO9906146 | A2 | 2/1999 |
| JP | 2006000451 | A | 1/2006 | WO | WO9906356 | | 2/1999 |
| JP | 2006511591 | A | 4/2006 | WO | WO9906359 | A1 | 2/1999 |
| JP | 2006519797 | A | 8/2006 | WO | WO9913983 | A1 | 3/1999 |
| JP | 2006528616 | A | 12/2006 | WO | WO9964155 | A1 | 12/1999 |
| JP | 2007083057 | A | 4/2007 | WO | WO0001485 | A2 | 1/2000 |
| JP | 2007509885 | A | 4/2007 | WO | WO0037431 | A1 | 6/2000 |
| JP | 2007509886 | A | 4/2007 | WO | WO0121684 | A1 | 3/2001 |
| JP | 2007509887 | A | 4/2007 | WO | WO0136429 | A1 | 5/2001 |
| JP | 2007519516 | A | 7/2007 | WO | WO0168247 | A2 | 9/2001 |
| JP | 2007519663 | A | 7/2007 | WO | WO0168247 | A8 | 9/2001 |
| JP | 2007519664 | A | 7/2007 | WO | WO0211108 | A1 | 2/2002 |
| JP | 2007519666 | A | 7/2007 | WO | WO0213964 | A2 | 2/2002 |
| JP | 2007519667 | A | 7/2007 | WO | WO0218392 | A1 | 3/2002 |
| JP | 2007519670 | A | 7/2007 | WO | WO0226698 | A1 | 4/2002 |
| JP | 2007519671 | A | 7/2007 | WO | WO0230854 | A2 | 4/2002 |
| JP | 2007519672 | A | 7/2007 | WO | WO02053527 | A1 | 7/2002 |
| JP | 2007519673 | A | 7/2007 | WO | WO02092551 | A2 | 11/2002 |
| JP | 2007519674 | A | 7/2007 | WO | WO03011457 | A1 | 2/2003 |
| JP | 2007519675 | A | 7/2007 | WO | WO03018540 | A1 | 3/2003 |
| JP | 2007519677 | A | 7/2007 | WO | WO03024919 | A1 | 3/2003 |
| JP | 2007522122 | A | 8/2007 | WO | WO03031392 | A1 | 4/2003 |
| JP | 04012248 | B2 | 11/2007 | WO | WO03033141 | A1 | 4/2003 |
| JP | 2006515323X | | 2/2008 | WO | WO03033509 | A1 | 4/2003 |

| | | | |
|---|---|---|---|
| WO | WO03046019 A1 | 6/2003 |
| WO | WO03046049 A1 | 6/2003 |
| WO | WO03068729 A1 | 8/2003 |
| WO | WO03076394 A1 | 9/2003 |
| WO | WO2004007431 A1 | 1/2004 |
| WO | WO2004007432 A1 | 1/2004 |
| WO | WO2004007435 A2 | 1/2004 |
| WO | WO2004007508 A2 | 1/2004 |
| WO | WO2004060855 A1 | 7/2004 |
| WO | WO2004064994 A2 | 8/2004 |
| WO | WO2004065352 A2 | 8/2004 |
| WO | WO2004080924 A2 | 9/2004 |
| WO | WO2004090848 A1 | 9/2004 |
| WO | WO2004087314 A1 | 10/2004 |
| WO | WO2005019160 A1 | 3/2005 |
| WO | WO2005042156 A1 | 5/2005 |
| WO | WO2005042157 A2 | 5/2005 |
| WO | WO2005042547 A1 | 5/2005 |
| WO | WO2005042549 A1 | 5/2005 |
| WO | WO2005073167 A1 | 8/2005 |
| WO | WO2005073168 A1 | 8/2005 |
| WO | WO2005073169 A1 | 8/2005 |
| WO | WO2005073170 A1 | 8/2005 |
| WO | WO2005073171 A1 | 8/2005 |
| WO | WO2005073172 A1 | 8/2005 |
| WO | WO2005073173 A1 | 8/2005 |
| WO | WO2005073174 A1 | 8/2005 |
| WO | WO2005073175 A1 | 8/2005 |
| WO | WO2005073176 A1 | 8/2005 |
| WO | WO2005073178 A2 | 8/2005 |
| WO | WO2005073179 A1 | 8/2005 |
| WO | WO2005073241 A1 | 8/2005 |
| WO | WO2006040023 A1 | 4/2006 |
| WO | WO2006042675 A2 | 4/2006 |
| WO | WO2005073166 A3 | 3/2007 |
| WO | WO2007096274 A1 | 8/2007 |
| WO | WO 2007115936 | 10/2007 |
| WO | WO2007115936 A2 | 10/2007 |
| WO | WO2008008928 A2 | 1/2008 |
| WO | WO2008008929 A2 | 1/2008 |
| WO | WO2008008930 A2 | 1/2008 |
| WO | WO2008028843 A1 | 3/2008 |
| WO | WO2008062058 A1 | 5/2008 |
| WO | WO2008008926 A2 | 7/2008 |

OTHER PUBLICATIONS

International Search Report for PCT/FR2004/000143 dated Sep. 1, 2004.
Summary Report: Control and Treatment for the Metal Finishing Industry—Ion Exchange USEPA EPA 625/-81-007 Jun. 1981 pp. 11-46.

* cited by examiner

METHOD OF PRODUCING DINITRILE COMPOUNDS

This application is an application under 35 U.S.C. Section 371 of International Application Number PCT/FR2004/000143 filed on Jan. 22, 2004.

The present invention relates to a process for the manufacture of compounds comprising two nitrile functional groups.

It relates more particularly to a process for the manufacture of dinitrile compounds from compounds comprising a nitrile functional group and an ethylenic unsaturation.

Dinitrile compounds, in particular adiponitrile, are important chemical intermediates in the synthesis of numerous compounds. Thus, adiponitrile is used in the manufacture of hexamethylenediamine, one of the monomers of polyamides. It can also be used in the manufacture of aminocapronitrile or caprolactam, monomers important in the production of various polyamides.

Among the processes provided for the synthesis of adiponitrile, the process using butadiene as starting material and the hydrocyanation reaction with hydrogen cyanide is the most extensively used industrially.

This process consists, in a first stage, in carrying out the hydrocyanation of an olefin, such as butadiene, to produce compounds comprising a nitrile functional group and an ethylenic unsaturation. This stage is generally carried out in the presence of a catalytic system comprising an organometallic complex formed by a metal, such as nickel, and an organophosphorus ligand.

After separation of the unsaturated mononitrile compounds and optionally purification, the latter are converted to dinitrile compounds by a second hydrocyanation reaction also carried out in the presence of a catalytic system comprising an organo-metallic complex formed by a metal, such as nickel, and an organophosphorus ligand. Furthermore, the catalytic system comprises a cocatalyst generally composed of a Lewis acid.

The term "Lewis acid" is understood to mean, according to the usual definition, compounds which accept electron pairs. Lewis acids are generally salts of metal elements, as is described below.

In the current processes, the Lewis acid is maintained in the reaction medium, in particular during the stage of extraction of the nitrites. The Lewis acid is subsequently removed with the distillation bottoms, in particular when it is not separated from the medium in conjunction with the organometallic complex used as catalytic system.

The presence of the Lewis acid during the distillation of the dinitrile can promote the generation of impurities in the medium, which impurities may be present in the distilled dinitrile. In addition, the removal of the Lewis acid and its discharge as effluent can be harmful to the economics of the process and to the environment. One of the aims of the present invention is to provide a process for the manufacture of dinitrile compounds which does not comprise these disadvantages.

To this end, the invention provides a process for the manufacture of dinitrile compounds by hydrocyanation with hydrogen cyanide of compounds comprising a nitrile functional group and an ethylenic unsaturation in the presence of a catalytic system comprising an organo-metallic complex and a cocatalyst formed by a metal compound.

According to the invention, the process comprises the following successive stages, after having carried out the hydrocyanation stage:

I. treating the reaction medium El obtained after the stage of hydrocyanation of the unsaturated nitrile compounds in order to extract at least the organometallic complex from said medium and to obtain a second medium $E_2$;

II. treating the said second medium $E_2$ by passing over an ion-exchange resin in order to extract at least the metal forming the cocatalyst and to obtain a third medium $E_3$, and III. separating the dinitriles formed from the said medium $E_3$, and in that the order of stages II) and III) can be reversed.

According to a preferred characteristic of the invention, the cocatalyst is a Lewis acid. More specifically, the Lewis acids mentioned in the work edited by G. A. Olah, "Friedel-Crafts and Related Reactions", Volume 1, pages 191 to 197 (1953), are suitable for the invention.

The Lewis acids which can be employed as cocatalysts in the present process are chosen from compounds of the elements from Groups Ib, IIb, IIIa, IIIb, IVa, IVb, Va, Vb, VIb, VIIb and VIII of the Periodic Table of the Elements. These compounds are generally salts, in particular halides, such as chlorides or bromides, sulphates, sulphonates, haloalkylsulphonates, perhaloalkylsulphonates, in particular fluoroalkylsulphonates or perfluoroalkylsulphonates, haloacetates, perhaloacetates, carboxylates and phosphates.

Mention may be made, as non-limiting examples of such Lewis acids, of zinc chloride, zinc bromide, zinc iodide, manganese chloride, manganese bromide, cadmium chloride, cadmium bromide, stannous chloride, stannous bromide, stannous sulphate, stannous tartrate, indium chloride, indium trifluoromethylsulphonate, indium trifluoroacetate, the chlorides or bromides of rare earth elements, such as lanthanum, cerium, praseodymium, neodymium, samarium, europium, gadolinium, terbium, dysprosium, hafnium, erbium, thallium, ytterbium and lutetium, cobalt chloride, ferrous chloride or yttrium chloride.

Use may also be made, as Lewis acid, of compounds such as triphenylborane or titanium isopropoxide.

It is possible, of course, to employ mixtures of several Lewis acids.

Preference is very particularly given, among Lewis acids, to zinc chloride, zinc bromide, stannous chloride, stannous bromide, triphenylborane, indium trifluoromethylsulphonate, indium trifluoroacetate and zinc chloride/stannous chloride mixtures.

The Lewis acid cocatalyst employed generally represents from 0.01 to 50 mol per mole of transition metal compound, more particularly of nickel compound.

According to a preferred embodiment of the invention, stage II) of treatment over ion-exchange resins is carried out before the separation of the dinitrile compounds from the medium $E_3$.

This is because the separation of the dinitrile compounds is generally carried out by distillation and thus by heating the medium $E_3$ comprising these compounds. It is advantageous to remove the metal elements present in the medium $E_3$ before carrying out such a heating in order to prevent these metal elements from promoting side reactions or decomposition of the dinitriles. These side or decomposition reactions generate by-products with a structure similar to that of the dinitriles which are difficult to separate from the latter.

Thus, in the case of adiponitrile, certain impurities, such as 1-imino-2-cyanocyclopentane (ICCP), can be produced. These impurities are reencountered in part in the distilled adiponitrile. The impurities and their hydrogenation products can also be reencountered in the hexamethylenediamine (HMD) obtained by hydrogenation of this adiponitrile and even in the polyamide obtained from the HMD.

Thus, these impurities can produce defects in the processes for forming these polyamides, in particular in spinning processes (increase in the number of breakages of the yarns) or with regard to the stability and the colour of the polyamide.

According to a preferred characteristic of the invention, the organometallic complex forming the catalytic system is generally a coordination complex between a metal element chosen from transition metals and ligands, generally organophosphorus ligands.

Such organometallic complexes are disclosed in numerous publications and numerous patents, such as U.S. Pat. No. 3,496,215, DE19953058, FR 1 529 134, FR 2 069 411, U.S. Pat. No. 3,631,191, U.S. Pat. No. 3,766,231, FR 2 523 974, WO 99/06355, WO 99/06356, WO 99/06357, WO 99/06358, WO 99/52632, WO 99/65506, WO 99/62855, U.S. Pat. No. 5,693,843, WO 96/1182, WO 96/22968, U.S. Pat. No. 5,981, 772, WO 01/36429, WO 99/64155 or WO 02/13964.

The metal elements are generally chosen from the group consisting of nickel, cobalt, iron, ruthenium, rhodium, palladium, osmium, iridium, platinum, copper, silver, gold, zinc, cadmium and mercury. Among these metals, nickel is the preferred metal.

In these metal complexes, the metal is encountered in a specific oxidation state, in particular zero for nickel, for example.

During the hydrocyanation reaction, a portion of the metal element (for example nickel) can be oxidized to a higher oxidation state, for example state 1 or 2, and may thus no longer be extractable from the reaction medium $E_1$ during stage I) of the process of the invention. Its presence in the reaction media $E_2$ or $E_3$ can result in disadvantages similar to those of the metal elements originating from the cocatalyst.

This disadvantage is overcome by the process of the invention, which makes it possible, according to a preferred characteristic, to coextract these metal elements during the stage II) of treatment over ion-exchange resins by choosing an appropriate resin and appropriate extraction conditions. It is also possible, without departing from the scope of the present invention, to use two or more resins in combination or successively in order to make possible the concomitant or successive extraction of these metal elements.

Mention may be made, as organometallic complexes suitable for the invention, of those obtained from nickel compounds and from organophosphorus compounds belonging to the families of the monodentate or polydentate organophosphites, organophosphinites, organophosphonites and organophosphines. It is also possible to use organometallic complexes obtained from stilbene or arsine in combination with nickel or one of the metals mentioned above. Examples of organophosphorus compounds are disclosed in numerous publications and numerous patents. Mention may be made, for example, as examples of monodentate compounds, of triphenyl phosphite, tritolyl phosphite, trithymyl phosphite, phenyl diphenylphosphinite, tolyl ditolylphosphinite, thymyl dithymylphosphinite, diphenyl phenylphosphonite, ditolyl tolylphosphonite, dithymyl thymylphosphonite, triphenylphosphine, tritolylphosphine or trithymylphosphine.

Mention may be made, as bidentate compounds, by way of examples, of the following structures, in which Ph indicates phenyl:

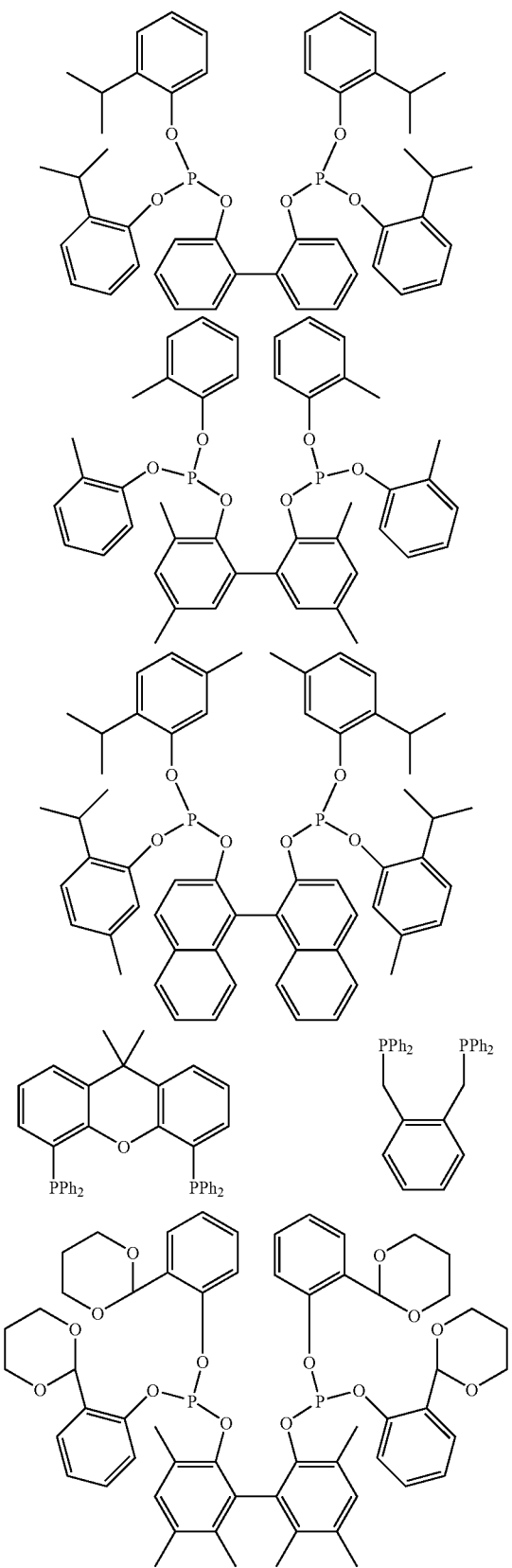

More generally, all organophosphorus ligands are suitable for the invention.

Mention may also be made, by way of examples, of the catalytic systems and ligands disclosed in patents WO 95/30680, WO 96/11182, WO 99/06358, WO 99/13983, WO 99/64155, WO 01/21579 and WO 01/21580.

The organometallic complexes can be prepared before their addition to the reaction medium or in situ.

The organometallic complexes can be prepared by bringing a compound of the chosen metal into contact with a solution of an organophosphorus compound.

The compound of the metal can be dissolved in a solvent.

The metal can be present in the compound employed either in the oxidation state which it will have in the organometallic complex or in a higher oxidation state.

By way of examples, it may be indicated that, in the organometallic complexes of the invention, rhodium is in the oxidation state (I), ruthenium is in the oxidation state (II), platinum is in the oxidation state (0), palladium is in the oxidation state (0), osmium is in the oxidation state (II), iridium is in the oxidation state (I) and nickel is in the oxidation state (0).

If, during the preparation of the organometallic complex, the metal is employed in a higher oxidation state, it can be reduced in situ.

Mention may be made, as nonlimiting examples of metal compounds used in the preparation of these complexes, of metal powders, such as nickel powder, and the following compounds:

compounds in which the nickel is in the zero oxidation state, such as potassium tetracyanonickelate $K_4[Ni(CN)_4]$, bis(acrylonitrile)nickel(0), bis(1,5-cyclooctadiene)nickel (also known as $Ni(cod)_2$) and the derivatives comprising ligands, such as tetrakis-(triphenylphosphine)nickel(0), nickel compounds, such as the carboxylates (in particular the acetate), carbonate, bicarbonate, borate, bromide, chloride, citrate, thiocyanate, cyanide, formate, hydroxide, hydrophosphite, phosphate, phosphate and derivatives, iodide, nitrate, sulphate, sulphite, arylsulphonates and alkylsulphonates.

When the nickel compound used corresponds to an oxidation state of the nickel of greater than 0, a reducing agent for the nickel is added to the reaction medium, which reducing agent preferably reacts with the nickel under the conditions of the reaction. This reducing agent can be organic or inorganic. Mention may be made, as nonlimiting examples, of borohydrides, such as $NaBH_4$ or $KBH_4$, Zn powder, magnesium or hydrogen.

When the nickel compound used corresponds to the 0 oxidation state of the nickel, a reducing agent of the type of those mentioned above can also be added but this addition is not essential.

When an iron compound is used, the same reducing agents are suitable.

In the case of palladium, the reducing agents can, in addition, be components of the reaction medium (phosphine, solvent, olefin).

The cocatalyst or Lewis acid is present in the catalytic system according to an amount of between 0.01 and 50 mol of Lewis acid per mole of metal element of the organometallic complex, such as nickel, for example, and preferably between 0.05 and 10 mol/mol. The Lewis acid can be added directly to the reaction medium or with the organometallic complex.

The hydrocyanation reaction is generally carried out at a temperature of between 10° C. and 200° C., preferably between 30° C. and 120° C.

The hydrocyanation reaction can be carried out without solvent but it can be advantageous to add an inert organic solvent. This solvent can be a solvent for the catalytic system which is miscible with the phase or with the medium comprising the compound to be hydrocyanated, at least at the hydrocyanation temperature.

This reaction and the process of the invention can be carried out continuously or batchwise.

This reaction can also be carried out in the presence of a two-phase system comprising in particular an aqueous phase in which the organometallic complex is soluble. In this embodiment, the aqueous phase is separated with most of the organometallic complex at the end of the reaction. The organic phase comprising the dinitriles and the unreacted unsaturated nitriles is the medium $E_1$ within the meaning of the present invention. This is because it is advantageous to treat this organic phase according to the process of the invention in order to extract the small portion of organic complex and of Lewis acid present in the said phase.

The reaction medium $E_1$ obtained at the outlet of the hydrocyanation reactor is, according to a preferred embodiment of the invention, fed to a stage I) for extraction of the organometallic complex.

This stage can consist of an extraction of the said complex by a solvent in a liquid/liquid extraction plant. Mention may be made, by way of examples, as extraction solvent, of alkanes comprising from 5 to 9 carbon atoms, such as pentane, hexane or heptane, cycloalkanes comprising from 5 to 8 carbon atoms, such as cyclohexane, methylcyclohexane or cyclooctane, halogenated hydrocarbons comprising from 1 to 5 carbon atoms, such as chloroform, dichloroethane, carbon tetrachloride, chloropropane or dichloromethane, or substituted or unsubstituted aromatic compounds comprising from 6 to 9 carbon atoms, such as benzene, toluene, xylene, ethylbenzene or isopropylbenzene.

This separation can also be brought about by distillation of the unsaturated nitriles and the production of a two-phase medium, one of the phases of which comprises the organometallic complex, the other phase of which comprising mainly the dinitriles. The latter can be subjected to liquid/liquid extraction with the solvents described above in order to extract the traces of organometallic complex.

The organometallic complex thus extracted can be recycled in a hydrocyanation reaction.

At the end of stage I), a reaction medium $E_2$ no longer comprising organometallic complex is obtained. The term "no longer comprises" should be understood as meaning that the maximum amount of the organometallic complex has been extracted but traces of the said complex may remain in the medium without, however, departing from the scope of the invention.

This reaction medium $E_2$ comprises the dinitriles formed and also the Lewis acid and optionally compounds of the metal element originating from the organometallic complex which may or may not have undergone oxidation.

According to the preferred embodiment of the invention, this reaction medium $E_2$ is subjected to a treatment over ion-exchange resins which makes it possible to fix and extract the metal ions of the Lewis acid and optionally the oxidized metal ions which originate from the organometalllc complex and which are found in the said medium $E_2$.

Suitable ion-exchange resins of the present invention are chosen according to the nature of the metal elements to be extracted. Thus, these resins can be one of those belonging to the group consisting of strong or weak cationic resins, adsorbent resins, chelating resins and catalytic resins. Mention may be made, as examples of resins, of sulphonic resins, carboxylic resins, iminodiacetic resins or resins sold under the tradenames AMBERLITE® and AMBERLYST® by Rohm & Haas, DOWEX® by Dow and LEVATITE® and IONAC® by Bayer.

This stage II) can be carried out in any device known to a person skilled in the art. Thus, use may be made of columns comprising these resins in the form of a fixed bed or of a fluidized bed or membrane systems formed by the said resin.

After treatment on a resin, a reaction medium $E_3$ is obtained which comprises essentially the dinitrile organic compounds formed. These various compounds will advantageously be separated in a distillation stage III). However, other separation processes can be used without, however, departing from the scope of the invention.

Furthermore, the stage II) of treatment with the resins also comprises a stage of elution of the resins laden with the extracted metal elements in order thus to regenerate the resins and to recover these metal elements.

This elution is a conventional and standard stage for processes for treatment on ion-exchange resins. It can be carried out in particular using strong acids, such as sulphuric acid or hydrochloric acid, or strong organic acids and preferably the acid corresponding to the anion of the Lewis acid to be regenerated.

In the context of the present invention, this elution stage can make it possible to recover and regenerate the Lewis acid and can thus make possible its reuse in a hydrocyanation stage. This possibility is of great advantage in making possible economical operation of the process and respect for the environment, in particular when the compound used as Lewis acid is expensive and/or exhibits a toxic nature with respect to the environment.

The process of the invention applies in particular to aliphatic nitriles comprising an ethylenic unsaturation and more particularly to linear pentenenitriles, such as 3-pentenenitrile or 4-pentenenitrile.

These pentenenitriles can comprise minor amounts of other compounds, such as 2-methyl-3-butenenitrile, 2-methyl-2-butenenitrile, 2-pentenenitrile, valero-nitrile, adiponitrile, 2-methylglutaronitrile or 2-ethylsuccinonitrile. These compounds are present in the pentenenitriles, in particular when the latter originate from a first stage of hydrocyanation of butadiene to give unsaturated mononitriles.

This first stage is generally carried out in the presence of a catalyst comprising an organometallic complex but in the absence of cocatalyst. The organo-metallic complex used in this first stage can be different from or identical to that used in the process of the invention. In the case where it is identical, the organometallic complex recovered in stage I) of the process of the invention can be recycled in the hydrocyanation reactor for the first stage of hydrocyanation of butadiene.

The mononitriles introduced in the process of the invention can also originate from an isomerization stage, generally in association with the first stage above, which consists in maintaining the compounds obtained in the first stage above in the presence of a catalytic system comprising an organometallic complex, advantageously identical to that of the first stage, in the absence of hydrogen cyanide.

This object of this isomerization stage is to improve the selectivity of the process for linear unsaturated mononitriles.

Other advantages and details of the invention will become more clearly apparent in the light of the examples given below solely by way of indication and of illustration.

EXAMPLE 1

A solution of indium trifluoroacetate (0.5 g, 1.10 mmol) in a mixture of 3-pentenenitrile (36.4 g, 448 mmol) and adiponitrile (63.6 g, 588 mmol) is prepared. The composition of the medium is determined by elemental analysis.

4 ml fractions of this solution are brought into contact with 2 ml of each of the following resins sold by Rohm & Haas under the tradenames indicated below:
a sulphonic resin (AMBERLITE® 252H),
a chelating resin (IRC 748),
an adsorbent resin (AMBERLITE® XAD7)
and a cationic resin (IRC 50).

Each of the media is stirred at ambient temperature (20° C.) for 4 h. The resin is separated by filtration and the composition of the filtrate is determined by elemental analysis.

The compositions of the starting media and of the filtrates are given in Table I below:

|  |  | In (ppm) |
| --- | --- | --- |
| Composition of the starting medium |  | 1190 |
| Composition of the filtrate | AMBERLITE ™ 252H Sulphonic resin | Undetectable |
|  | IRC 748 Chelating resin | Undetectable |
|  | AMBERLITE ™ XAD7 Adsorbent resin | Undetectable |
|  | IRC 50 Cationic resin | Undetectable |

EXAMPLE 2

A glass column is filled with 100 ml of sulphonic resin (AMBERLITE® 252H). A solution of 3-pentenenitrile and of adiponitrile (30/70 in moles) comprising indium trifluoroacetate with a concentration, expressed as indium element, of 3300 ppm is fed continuously via the top of the column at a flow rate of 340 g/h. Samples are withdrawn every 10 minutes at the column outlet. The concentration of indium in the samples is measured by elemental analysis.

During the three hours of operation of the separating column, the concentration of resin in the samples was always less than 20 ppm.

EXAMPLE 3

A solution of zinc chloride (0.1 g, 0.73 mmol) in a mixture of 3-pentenenitrile (36.4 g, 448 mmol) and of adiponitrile (63.6 g, 588 mmol) is prepared. The composition of the medium is determined by elemental analysis.

4 ml of this solution are stirred at ambient temperature (20° C.) for 4 h in the presence of 2 ml of sulphonic resin (AMBERLITE® 252H). Analysis of the solution before and after treatment over resin indicates that the concentration of zinc in the solution changes from 480 ppm to 8 ppm.

EXAMPLE 4

The reaction for the hydrocyanation of 3-pentenenitrile to give adiponitrile, catalyzed by the Ni(0)/organophosphorus ligand/Lewis (In) acid system, is carried out. The organophosphorus ligand is the compound with the following formula:

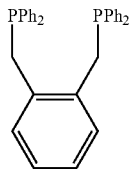

3 ml fractions of this reaction medium are stirred at ambient temperature (approximately 20° C.) for 4 hours in the presence of 3 ml of one of the following resins:
a sulphonic resin (AMBERLITE® 252H),
a chelating resin (IRC 748),
an adsorbent resin (AMBERLITE® XAD7).

The composition of the reaction medium before and after treatment over resin is given in Table II below:

|  | Resin ref. | % Ni | % In |
|---|---|---|---|
| Starting composition | / | 0.459 | 1.0 |
| Composition after treatment | AMBERLITE ™ 252H | 0.46 | <0.02 |
|  | AMBERLITE ™ XAD-7 | 0.28 | 0.42 |
|  | IRC 748 | <0.008 | <0.17 |

These tests show that it is possible to extract the indium originating from the Lewis acid but also, under certain conditions, the oxidized nickel originating from the organometallic complex used as catalyst.

The invention claimed is:

1. A process for the manufacture of dinitrile compounds by hydrocyanation of mononitrile compounds comprising an ethylenic unsaturation by reaction with hydrogen cyanide in the presence of a catalytic system comprising an organometallic complex and a cocatalyst comprising metal ions, said process comprising the following successive steps:
   I) separating the organometallic complex from a liquid reaction medium $E_1$ obtained after hydrocyanation of unsaturated nitrile compounds and obtaining a second liquid medium $E_2$ comprising dinitriles and metal ions originating from the cocatalyst,
   II) extracting from the second liquid medium $E_2$ metal ions originating from the cocatalyst with an ion-exchange resin and obtaining a third medium $E_3$ comprising dinitriles, and
   III) separating the dinitriles from the third medium $E_3$.

2. The process according to claim 1, wherein the cocatalyst is a Lewis acid.

3. The process according to claim 1, wherein the metal ions extracted in step II) are recovered by elution from the resin.

4. The process according to claim 3, wherein the metal ions recovered are recycled in order to form the cocatalyst of the catalytic system of the hydrocyanation stage.

5. The process according to claim 2, wherein the Lewis acid is a compound of a metal element belonging to Group Ib, IIb, IIIa, IIIb, IVa, IVb, Va, Vb, VIb, VIIb or VIII of the Periodic Table of the Elements.

6. The process according to claim 2, wherein the Lewis acid is selected from the group consisting of halides, sulphates, sulphonates, haloalkylsulphonates, perhaloalkylsulphonates, haloacetates, perhaloacetates, carboxylates and phosphates of the metal elements.

7. The process according to claim 6, wherein the Lewis acid is selected from the group consisting of chlorides, bromides, fluoroalkylsulphonates and perfluoroalkylsulphonates.

8. The process according to claim 2, wherein the Lewis acid is zinc chloride, zinc bromide, zinc iodide, manganese chloride, manganese bromide, cadmium chloride, cadmium bromide, stannous chloride, stannous bromide, stannous sulphate, stannous tartrate, indium chloride, indium trifluoromethylsulphonate, indium trifluoroacetate, cobalt chloride, ferrous chloride or yttrium chloride.

9. The process according to claim 2, wherein the Lewis acid is a chloride or a bromide of a rare earth element selected from the group consisting of lanthanum, cerium, praseodymium, neodymium, samarium, europium, gadolinium, terbium, dysprosium, hafnium, erbium, thallium, ytterbium and lutetium.

10. The process according to claim 1, wherein the resin for extraction of the metal ions used in step II) is a weak cationic resin, a strong cationic resin, an adsorbent resin, a chelating resin or a catalytic resin.

11. The process according to claim 10, wherein the ion-exchange resin is a sulphonic resin, carboxylic resin or iminodiacetic resin.

12. The process according to claim 1, wherein the separation of the organometallic complex in step I) is carried out by liquid/liquid extraction with an extraction solvent chosen from the group consisting of alkanes comprising from 5 to 9 carbon atoms, cycloalkanes comprising from 5 to 8 carbon atoms, halogenated hydrocarbons comprising from 1 to 5 carbon atoms, substituted aromatic compounds comprising from 6 to 9 carbon atoms and or unsubstituted aromatic compounds comprising from 6 to 9 carbon atoms.

13. The process according to claim 1, wherein the separation of the dinitriles in step III) is carried out by distillation of said dinitriles.

14. The process according to claim 1, wherein said process is for the manufacture of adiponitrile, and wherein the unsaturated mononitrile compounds are pentenenitriles.

15. The process according to claim 14, wherein the pentenenitriles are obtained by hydrocyanation of butadiene.

16. The process according to claim 1, wherein said organometallic complex is an organometallic phosphite complex.

17. The process according to claim 1, wherein said extraction step II) is carried out at ambient temperature.

18. A process for the manufacture of dinitrile compounds by hydrocyanation of mononitrile compounds comprising an ethylenic unsaturation by reaction with hydrogen cyanide in the presence of a catalytic system comprising an organometallic complex and a cocatalyst comprising metal ions, said process comprising the following successive steps:
   I) separating the organometallic complex from a liquid reaction medium $E_1$ obtained after hydrocyanation of unsaturated nitrile compounds and obtaining a second liquid medium $E_2$ comprising dinitriles and metal ions originating from the cocatalyst,
   IIa) separating the dinitriles by distillation from the second liquid medium $E_2$, wherein the distillation bottoms comprise said metal ions originating from the cocatalyst, and
   III a) extracting from the distillation bottoms of step IIa) metal ions originating from the cocatalyst with an ion-exchange resin.

19. The process according to claim 18, wherein the metal ions extracted in step IIIa) are recovered by elution from the resin.

20. The process according to claim 18, wherein said extraction step IIIa) is carried out at ambient temperature, and wherein said organometallic complex is an organometallic phosphite complex.

* * * * *